US010064591B2

(12) United States Patent
Wang et al.

(10) Patent No.: US 10,064,591 B2
(45) Date of Patent: Sep. 4, 2018

(54) SYSTEM, METHOD AND COMPUTER READABLE MEDIUM FOR PREVIEW OF LOW-DOSE X-RAY PROJECTION AND TOMOGRAPHIC IMAGES

(71) Applicant: The Johns Hopkins University, Baltimore, MD (US)

(72) Inventors: Adam Wang, Baltimore, MD (US); Jeffrey H. Siewerdsen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 54 days.

(21) Appl. No.: 15/322,697

(22) PCT Filed: Jul. 9, 2015

(86) PCT No.: PCT/US2015/039782
§ 371 (c)(1),
(2) Date: Dec. 28, 2016

(87) PCT Pub. No.: WO2016/007769
PCT Pub. Date: Jan. 14, 2016

(65) Prior Publication Data
US 2017/0135659 A1     May 18, 2017

Related U.S. Application Data

(60) Provisional application No. 62/022,551, filed on Jul. 9, 2014.

(51) Int. Cl.
*A61B 6/00*     (2006.01)
*A61B 6/02*     (2006.01)
(Continued)

(52) U.S. Cl.
CPC ............... *A61B 6/488* (2013.01); *A61B 6/02* (2013.01); *A61B 6/4233* (2013.01); *A61B 6/461* (2013.01);
(Continued)

(58) Field of Classification Search
CPC ....... A61B 6/032; A61B 6/488; A61B 6/5258; A61B 6/461; A61B 6/542; A61B 6/02;
(Continued)

(56) References Cited

U.S. PATENT DOCUMENTS

2008/0118128 A1*   5/2008   Toth ..................... G06T 11/003
                                                                                382/131
2012/0155609 A1    6/2012   Lemminger et al.
(Continued)

FOREIGN PATENT DOCUMENTS

EP             1444952 A1     8/2004
WO    WO-2014-036473 A1     3/2014

OTHER PUBLICATIONS

Benson et al., "Synthetic CT noise emulation in the raw data domain," in Nuclear Science Symposium Conference Record (NSS/MIC), 2010 IEEE(IEEE, 2010), pp. 3169-3171.
(Continued)

*Primary Examiner* — Kenny Cese
(74) *Attorney, Agent, or Firm* — Venable, LLP; Henry J. Daley

(57) ABSTRACT

A novel method for simulating radiation dose reduction that enables previews of low-dose x-ray projection images, low-dose computed tomography images and/or cone-beam CT images. Given an existing projection or set of projections of the patient acquired at a nominal dose, the method provides a means to produce highly accurate preview images that accurately reflect the image quality associated with reduced radiation dose. The low-dose preview image accounts for
(Continued)

characteristics of the imaging system, including blur, variations in detector gain and electronic noise, and does so in a manner that yields accurate depiction of the magnitude and correlation of image noise in the preview images. A calibration step may be included to establish the system-specific relationship between the mean and variance in detector signal, and incorporate an accurate model for system blur such that correlations in the resulting LDP images are accurate.

30 Claims, 9 Drawing Sheets

(51) Int. Cl.
    A61B 6/03          (2006.01)
    G06T 11/00        (2006.01)
(52) U.S. Cl.
    CPC ............ *A61B 6/5258* (2013.01); *A61B 6/542* (2013.01); *A61B 6/582* (2013.01); *A61B 6/032* (2013.01); *G06T 11/003* (2013.01); *G06T 2207/10081* (2013.01)
(58) Field of Classification Search
    CPC .................. A61B 6/4233; A61B 6/582; G06T 2207/10081; G06T 11/005; G06T 11/003
    See application file for complete search history.

(56) References Cited

U.S. PATENT DOCUMENTS

| | | | |
|---|---|---|---|
| 2013/0108130 A1 | 5/2013 | Nukui | |
| 2013/0148782 A1 | 6/2013 | Tajima | |
| 2015/0201895 A1* | 7/2015 | Suzuki | A61B 6/488 382/131 |

OTHER PUBLICATIONS

Britten, "The addition of computer simulated noise to investigate radiation dose and image quality in images with spatial correlation of statistical noise: an example application to X-ray CT of the brain," British Journal of Radiology 77(916), pp. 323-328 (2004).
Daly et al., "Geometric calibration of a mobile C-arm for intraoperative cone-beam CT," Medical physics 35, pp. 2124-2136 (2008).
Daly et al., "Intraoperative cone-beam CT for guidance of head and neck surgery: Assessment of dose and image quality using a C-arm prototype," Medical physics 33, pp. 3767-3780 (2006).
De Man et al., "Distance-driven projection and backprojection in three dimensions," Physics in Medicine and Biology 49(11), pp. 2463-2475 (2004).
Erdogan et al., "Monotonic algorithms for transmission tomography," IEEE Transactions on Medical Imaging 18(9), pp. 801-814 (1999).
Erdogan et al., "Ordered subsets algorithms for transmission tomography," Physics in Medicine and Biology 44(11), pp. 2835-2851 (1999).
Fahrig et al., "Use of a C-arm system to generate true three-dimensional computed rotational angiograms: preliminary in vitro and in vivo results," American Journal of Neuroradiology 18(8), pp. 1507-1514 (1997).
Feldkamp et al., "Practical cone-beam algorithm," JOSA A 1(6), pp. 612-619 (1984).
Frush et al., "Computer-simulated radiation dose reduction for abdominal multidetector CT of pediatric patients," American Journal of Roentgenology 179(5), pp. 1107-1113 (2002).
Galigekere et al., "Cone-beam reprojection using projection-matrices," Medical Imaging, IEEE Transactions on 22(10), pp. 1202-1214 (2003).
Hanai et al., "Computer-simulation technique for low dose computed tomographic screening.," Journal of computer assisted tomography 30(6), pp. 955-961 (2006).
Jaffray et al., "Flat-panel cone-beam computed tomography for image-guided radiation therapy," International Journal of Radiation Oncology Biology Physics 53(5), pp. 1337-1349 (2002).
Jia et al., "GPU-based iterative cone-beam CT reconstruction using tight frame regularization," Physics in Medicine and Biology 56(13), pp. 3787-3807 (2011).
Joemai et al., "Development and validation of a low dose simulator for computed tomography.," European radiology 20(4), pp. 958-966 (2010).
Kijewski et al., "The noise power spectrum of CT images," Physics in Medicine and Biology 32(5), pp. 565-575 (1987).
Kim et al., "Realistic simulation of reduced-dose CT with noise modeling and sinogram synthesis using DICOM CT images," Medical Physics 41(1), pp. 011901-1-01191-16 (2014).
Long et al., "3D forward and back-projection for X-ray CT using separable footprints," Medical Imaging, IEEE Transactions on 29(11), pp. 1839-1850 (2010).
Massoumzadeh et al., "Validation of CT dose-reduction simulation," Medical Physics 36(1), pp. 174-189 (2009).
Mayo et al., "Simulated dose reduction in conventional chest CT: validation study.," Radiology 202(2), pp. 453-457 (1997).
Miracle et al., "Conebeam CT of the head and neck, part 2: clinical applications," American Journal of Neuroradiology 30(7), pp. 1285-1292 (2009).
Navab et al., "Dynamic geometrical calibration for 3D cerebral angiography," in Proceedings of SPIE(1996), pp. 361-370.
Orth et al., "C-arm cone-beam CT: general principles and technical considerations for use in interventional radiology.," Journal of vascular and interventional radiology: JVIR 19(6), pp. 814-820 (2008).
Riederer et al., "The noise power spectrum in computed X-ray tomography," Physics in Medicine and Biology 23(3), pp. 446-454 (1978).
Schafer et al., "Mobile C-arm cone-beam CT for guidance of spine surgery: Image quality, radiation dose, and integration with interventional guidance," Medical physics 38, pp. 4563-4574 (2011).
Schmidgunst et al., "Calibration model of a dual gain flat panel detector for 2D and 3D x-ray imaging," Medical physics 34, pp. 3649-3664 (2007).
Siddon, "Prism representation: a 3D ray-tracing algorithm for radiotherapy applications," Physics in Medicine and Biology 30(8), pp. 817-824 (1985).
Sidky et al., "Image reconstruction in circular cone-beam computed tomography by constrained, total-variation minimization.," Physics in medicine and biology 53(17), pp. 4777-4807 (2008).
Siewerdsen et al., "A framework for noise-power spectrum analysis of multidimensional images," Medical Physics 29(11), pp. 2655-2671 (2002).
Siewerdsen et al., "Signal, noise power spectrum, and detective quantum efficiency of indirect-detection flat-panel imagers for diagnostic radiology," Medical Physics 25(5), pp. 614-628 (1998).
Siewerdsen et al., "Volume CT with a flat-panel detector on a mobile, isocentric C-arm: Pre-clinical investigation in guidance of minimally invasive surgery," Medical Physics 32(1), pp. 241-254 (2005).
Stayman et al., "Model-based tomographic reconstruction of objects containing known components.," IEEE transactions on medical imaging 31(10), pp. 1837-1848 (2012).
Strauss et al., "The ALARA (As Low As Reasonably Achievable) Concept in Pediatric Interventional and Fluoroscopic Imaging: Striving to Keep Radiation Doses as Low as Possible during Fluoroscopy of Pediatric Patients—A White Paper Executive Summary," Radiology 240(3), pp. 110-112 (2006).
Söderberg et al., "Simulated dose reduction by adding artificial noise to measured raw data: a validation study.," Radiation protection dosimetry 139(1-3), pp. 71-77 (2010).

(56) References Cited

OTHER PUBLICATIONS

Tang et al., "Performance comparison between total variation (TV)-based compressed sensing and statistical iterative reconstruction algorithms," Physics in Medicine and Biology 54(19), pp. 5781-5804 (2009).

Tsiklakis et al., "Dose reduction in maxillofacial imaging using low dose cone beam CT," European Journal of Radiology 56(3), pp. 413-417 (2005).

Tu et al., "Noise simulation in cone beam CT imaging with parallel computing.," Physics in medicine and biology 51(5), pp. 1283-1297 (2006).

Tward et al., "Cascaded systems analysis of the 3D noise transfer characteristics of flat-panel cone-beam CT," Medical Physics 35(12), pp. 5510-5529 (2008).

Veldkamp et al., "A technique for simulating the effect of dose reduction on image quality in digital chest radiography.," Journal of digital imaging 22(2), pp. 114-125 (2009).

Wallace et al., "Three-dimensional C-arm cone-beam CT: applications in the interventional suite," Journal of Vascular and Interventional Radiology 20(75), pp. S523-S537 (2008).

Wang et al., "Dose reduction for kilovotage cone-beam computed tomography in radiation therapy," Physics in Medicine and Biology 53(11), pp. 2897-2909 (2008).

Wang et al., "Image-based synthetic CT: simulating arbitrary low dose single and dual energy protocols from dual energy images," in Proceedings of SPIE(2012), pp. 83131G-1-83131G-7.

Wang et al., "Penalized weighted least-squares approach to sinogram noise reduction and image reconstruction for low-dose X-ray computed tomography," IEEE Transactions on Medical Imaging 25(10), pp. 1272-1283 (2006).

Wang et al., "Soft-tissue imaging with C-arm cone-beam CT using statistical reconstruction," Physics in Medicine and Biology 59(4), pp. 1005-1029 (2014).

Wang et al., "Synthetic CT: Simulating arbitrary single and dual energy protocols from a dual energy scan," Medical Physics 38(10), pp. 5551-5562 (2011).

Wu et al., "GPU acceleration of 3D forward and backward projection using separable footprints for X-ray CT image reconstruction," in Proc. of Fully 3D Image Reconstruction(2011), pp. 56-59.

Yu et al., "Development and validation of a practical lower-dose-simulation tool for optimizing computed tomography scan protocols.," Journal of computer assisted tomography 36(4), pp. 477-487 (2012).

Žabić et al., "A low dose simulation tool for CT systems with energy integrating detectors," Medical Physics 40, pp. 31102-1-31102-14 (2013).

International Search Report in International Application No. PCT/US2015/039782, dated Oct. 22, 2015.

\* cited by examiner

SYSTEM, METHOD AND COMPUTER READABLE MEDIUM FOR PREVIEW OF LOW-DOSE X-RAY PROJECTION AND TOMOGRAPHIC IMAGES

CROSS REFERENCE TO RELATED APPLICATIONS

This application is a U.S. National Stage Application under 35 U.S.C. § 371 of PCT/US2015/039782, filed on Jul. 9, 2015, and claims priority to U.S. Patent Application No. 62/022,551, filed Jul. 9, 2014, which is hereby incorporated by reference in its entirety.

FEDERAL FUNDING

This invention was made with Government support under 1F32EB017571, awarded by the Department of Health and Human Services, The National Institutes of Health (NIH). The U.S. Government has certain rights in the invention.

BACKGROUND

All references cited anywhere in this specification are incorporated herein by reference.

Cone-beam CT (CBCT) is finding increased application in areas such as image-guided surgery (IGS), image-guided radiation therapy (IGRT), and interventional radiology. In many of these applications, repeat CBCT scans are often acquired. For example, in IGS, an initial CBCT may be used for patient setup and registration of preoperative planning information, while subsequent CBCTs may be used for visualizing surgical progress, detection of complications, and/or verifying the surgical product. Additionally, in IGRT, patients may receive a CBCT scan at each treatment fraction. In accordance with efforts to reduce radiation dose to the patient (and in some cases to the clinicians, as with IGS), each CBCT should be acquired at the minimum dose such that a particular imaging task(s) can still be reliably performed. For scenarios in which multiple CBCTs of a patient are acquired, ensuring that each scan is conducted at the minimum dose sufficient for a given imaging task is especially important in reducing the total accumulated dose, since a fractional dose reduction per scan is multiplicative with the number of scans. Of course, lower dose techniques generally produce higher noise images, and selection of the minimum-dose protocol for a particular patient is challenging—usually guided simply by a coarse technique chart in which scan protocols are simply stratified by patient body habitus. The ability to confidently select low-dose protocols sufficient for a given imaging task and patient is therefore a challenge, and perhaps even more so for nonlinear model-based image reconstruction (MBIR) methods for which complex dose-noise-resolution tradeoffs may defy a simple predictive model.

Typically, a method utilized to aid in selecting a patient- and task-specific protocol (i.e., acquisition technique, image reconstruction method, and image processing/post-processing parameters) is to provide a "low-dose preview" (LDP) of the image quality that can be expected for a CBCT image acquired at reduced dose. This allows the user to visualize image quality at a particular reduced dose and confidently select a minimum-dose protocol sufficient for the imaging task.

More recently, simulated dose reduction methods have utilized models of noise beyond just quantum noise, such as the inclusion of electronic noise, which led to accurate reproduction of not only image noise magnitude but also noise power spectra. Other extensions of simulated dose reduction include using dual energy scans to allow simulated changes in tube voltage or using an image-based approach that does not assume availability of projection data (but does not allow for different reconstruction methods/parameters). Common to these methods is the assumption of spatially uncorrelated noise in the projection data, which may be a fair assumption for detectors employed in multi-detector CT scanners.

However, correlated noise is an important consideration for flat-panel detectors (FPDs) that are typically used in CBCT—for example, scintillator blur is known to introduce spatial correlation in the quantum noise, and electronic noise can be an important source of noise at very low dose levels. Therefore, previous methods for low-dose simulation in CT cannot be directly extended to CBCT based on indirect-detection FPDs since they do not include the effect of correlated noise (quantum or electronic noise).

SUMMARY

An embodiment of the invention is directed to a low-dose x-ray preview image method. The method is comprised of: (i) performing, by at least one processor, an initial scan of a patient at a pre-selected amount of x-ray exposure with an x-ray imaging device, (ii) creating, by the at least one processor, at least one initial image projection of said patient based on said initial scan, (iii) injecting, by the at least one processor, correlated noise into said at least one initial image projection of said initial scan of said patient, (iv) reconstructing, by at least one processor, said at least one initial image projection according to an algorithm specific to a task of said patient and based of said detected signal and said injecting of said correlated noise, (v) displaying, by at least one processor, at least one low-dose preview image based on said reconstruction of said at least one initial image projection according to an algorithm specific to a task of said patient and based on said detected signal and said injecting of said correlated noise, and (v) enabling, by at least one processor, a selection of said at least one low-dose preview image based on said at least one initial image projection according to an algorithm specific to a task of said patient and based on said detected signal and said injecting of said correlated noise for at least one subsequent scan.

Another embodiment of the current invention is directed to a low-dose x-ray preview image device. The device is comprised of: (i) an x-ray imaging device, (ii) at least one storage unit in communication with said x-ray imaging device, (iii) at least one data processor in communication with said at least one storage unit and said x-ray imaging device, and (iv) at least one display device in communication with said at least one storage unit and said at least one data processor. The device calls for the at least one processor to be configured to: (i) perform an initial scan of a patient at a pre-selected amount of x-ray exposure with said x-ray imaging device, (ii) create at least one initial preview image of said patient based on said initial scan, (iii) inject correlated noise into said at least one initial image projection of said initial scan of said patient, (iv) reconstruct said at least one initial image projection according to an algorithm specific to a task of said patient and based on said detected signal and said injecting of said correlated noise, (v) display, at said at least one display device, an at least one low-dose preview image based on said reconstruction of said at least one initial image projection according to an algorithm specific to a task of said patient and based on said detected signal and said injecting of said correlated noise, and (vi) enable, at said at least one display device, a selection of said at least one low-dose preview image based on said at least one initial image projection according to an algorithm specific to a task of said patient and based on said detected signal and said injecting of said correlated noise for at least one subsequent scan.

Yet another embodiment of the current invention is directed to a non-transitory computer readable medium. The non-transitory computer readable medium comprises which when executed by a computer, causes the computer to: (i) perform, by at least one processor, an initial scan of a patient at a pre-selected amount of x-ray exposure with an x-ray imaging device, (ii) create, by the at least one processor, at least one initial image projection of said patient based on said initial scan, (iii) inject, by the at least one processor, correlated noise into said at least one initial image projection of said initial scan of said patient, (iv) reconstruct, by at least one processor, said at least one initial image projection according to an algorithm specific to a task of said patient and based said detected signal and said injecting of said correlated noise, (vii) display, by at least one processor, at least one low-dose preview image based on said reconstruction of said at least one initial image projection according to an algorithm specific to a task of said patient and based on said detected signal and said injecting of said correlated noise, and (viii) enable, by at least one processor, a selection of said at least one low-dose preview image based on said at least one initial image projection according to an algorithm specific to a task of said patient and based on said detected signal and said injecting of said correlated noise for at least one subsequent scan.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

This invention is directed to a novel method and apparatus to accurately depict image quality for subsequent scans of a lower dose of x-ray exposure from an x-ray imaging device than an initial reference scan, including the faithful reproduction of spatial resolution, contrast, noise, and NPS characteristics. The method and apparatus operate directly on the initial reference projections data; therefore, the amount of x-ray exposed can be freely adjusted, and any reconstruction method and smoothing/regularization parameter selection can be applied. As a result, a plurality of low-dose preview images may be generated to illustrate the image quality that may result from the subsequent scans at a lower dose of x-ray exposure.

Accordingly, in using the observer's own preferences to select the minimum-dose protocol for a particular imaging task, this approach to prospective protocol selection is independent of models of observer performance; moreover, by operating on the actual projection data from the initial scan, it is patient-specific and applicable to advanced image reconstruction and processing methods.

Figure 1:
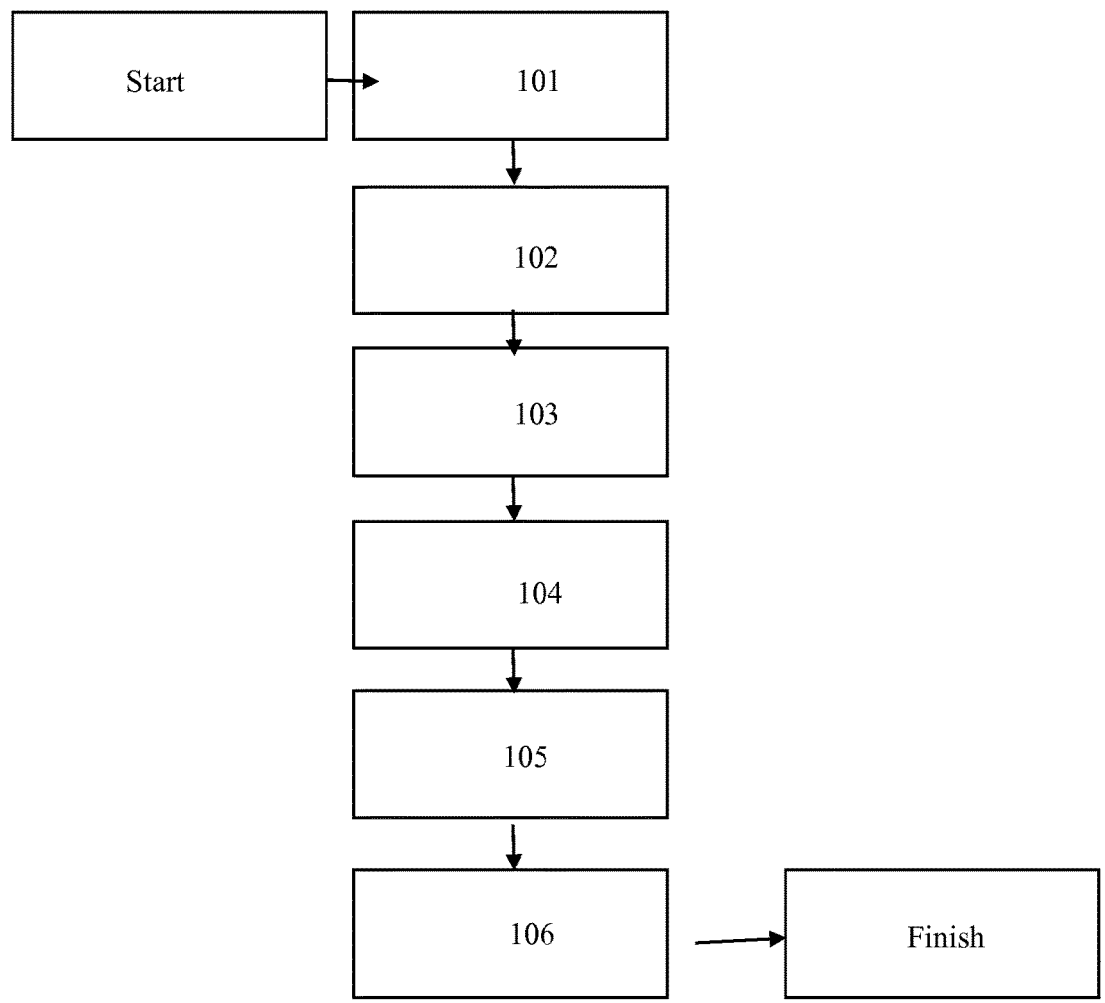
FIG. 1 illustrates an exemplary low-dose x-ray preview image method according to an embodiment of the invention.

Referring now to FIG. 1, an exemplary low-dose x-ray preview image method is illustrated according to an embodiment of the current invention. First, at block 101, at least one process performs an initial scan of a patient at a pre-selected amount of x-ray exposure with an x-ray imaging device. The x-ray imaging device may include at least an emitter and a detector. The detector is preferably a flat panel detector (FPD).

Thereafter, at block 102, the processor, creates at least one initial image projection of the patient based on the initial scan. The user, at block 103, may then inject, by the at least one processor, at least one amount of correlated noise into the at least one initial image projection of the initial scan of the patient.

The correlated noise injected into the at least one initial image projection of the initial scan of the patient represents a lower amount of x-ray exposure than the initial scan of the patient at the pre-selected amount of x-ray exposure. The correlated noise may include noise other than purely random noise. For example, the correlated noise may include at least one of, or both of, quantum noise and electronic noise. In addition, the correlated noise may also include the spatial correlation of at least one, or both of, the quantum and electronic noise, which in turn affects the reconstructed image.

Thereafter, at block 104, the at least one initial image projection is reconstruction according to an algorithm specific to a task of the patient and based on the detected signal and the injection of the correlated noise. The reconstruction of the at least one initial image projection includes at least one of, or both of, a filtered backprojection and a model-based image reconstruction.

Further, the at least one initial image may be modified in a manner that simulates tube output (given by the tube current-time product, units of mAs) reduction. When the tube output is reduced by a factor of $\alpha<1$ (i.e., exposure of the low-dose technique relative to that of the initial technique), the mean signal is reduced in proportion to $\alpha$, and the signal-to-noise ratio (SNR) is also reduced. Simulation of LDP projections $I_{LDP}$ from initial projections $I_{init}$ therefore comprises two main steps: 1) scaling the detected signal, and 2) injecting noise $n_{inject}$ into the projection. The overall relationship is expressed as:

$$I_{LDP}(u,v) = \alpha I_{init}(u,v) + n_{inject}(u,v), \quad (1)$$

where (u, v) is the pixel position. Scaling the initial projections ensures that the patient position, spatial resolution, x-ray energy, beam hardening, and scatter-to-primary ratio are preserved, while the addition of noise simulates tube output reduction but does not affect these other properties. Note that the first step of scaling the initial projections by $\alpha$ assumes detector linearity (a reasonable assumption for a well-calibrated detector) and image acquisition at the same x-ray energy (tube voltage (kVp) and filtration).

Accurate estimation of the injected noise $n_{inject}$ requires a model for both the magnitude and correlation of the quantum and electronic noise. From Eq. (1) the variance in the LDP projection is related to that in the initial projection and the injected variance by:

$$\sigma_{LDP}^2(u,v) = \alpha^2 \sigma_{init}^2(u,v) + \sigma_{inject}^2(u,v) \quad (2)$$

The initial scan is in turn reconstructed by whatever algorithm and post-processing methods are available in the imaging system.

The notation $I(.)$ denotes a projection image, $n(.)$ denotes a zero-mean noise realization, and $\sigma(.)$ denotes a noise map (alternatively $\sigma^2(.)$ a variance map). In Eq. (2), therefore, dose reduction is seen to scale the initial variance by $\alpha^2$, and the injected noise is assumed to be independent of $\sigma_{init}$. The system-specific signal-to-variance relationship is determined by a simple calibration detailed below. Each term in Eq. (2) represents the sum of two main sources of noise in x-ray imaging—quantum and electronic—which are assumed to be independent. For example, the first two terms of Eq. (2) can be written as a sum of quantum and electronic noise (subscripts q and e, respectively):

$$\sigma_{LDP}^2(u,v) = \sigma_{q,LDP}^2(u,v) + \sigma_{e,LDP}^2(u,v), \quad (3a)$$

$$\sigma_{init}^2(u,v) = \sigma_{q,init}^2(u,v) + \sigma_{e,init}^2(u,v). \quad (3b)$$

After substituting Eqs. (3) into Eq. (2) and rearranging terms, the injected variance can be written:

$$\sigma_{inject}^2(u,v) = (\sigma_{q,LDP}^2(u,v) - \alpha^2 \sigma_{q,init}^2(u,v)) + (\sigma_{e,LDP}^2(u,v) - \alpha^2 \sigma_{e,init}^2(u,v)) \quad (4)$$

The injected noise can also be represented by two components, which are defined to be the quantum and electronic injected variance:

$$\sigma_{q,inject}^2(u,v) \triangleq \sigma_{q,LDP}^2(u,v) - \alpha^2 \sigma_{q,init}^2(u,v), \quad (5a)$$

$$\sigma_{e,inject}^2(u,v) \triangleq \sigma_{e,LDP}^2(u,v) - \alpha^2 \sigma_{e,init}^2(u,v). \quad (5b)$$

The two components comprise the total injected variance:

$$\sigma_{inject}^2(u,v) = \sigma_{q,inject}^2(u,v) - \sigma_{e,inject}^2(u,v) \quad (6)$$

as in Eq. (4). The method for evaluating the injected quantum noise [Eq. (5a)] and injected electronic noise [Eq. (5b)] is explained below.

For example, in a particular exemplary embodiment, the same dose reduction factor $\alpha$ was applied to all projections of a scan, but the LDP method can similarly allow for tube current modulation by applying different $\alpha \leq 1$ to each projection according to the desired modulation. In another embodiment, LDP could be used to simulate dose reduction via sparse projection acquisition by discarding a subset of the projections.

Figure 2:
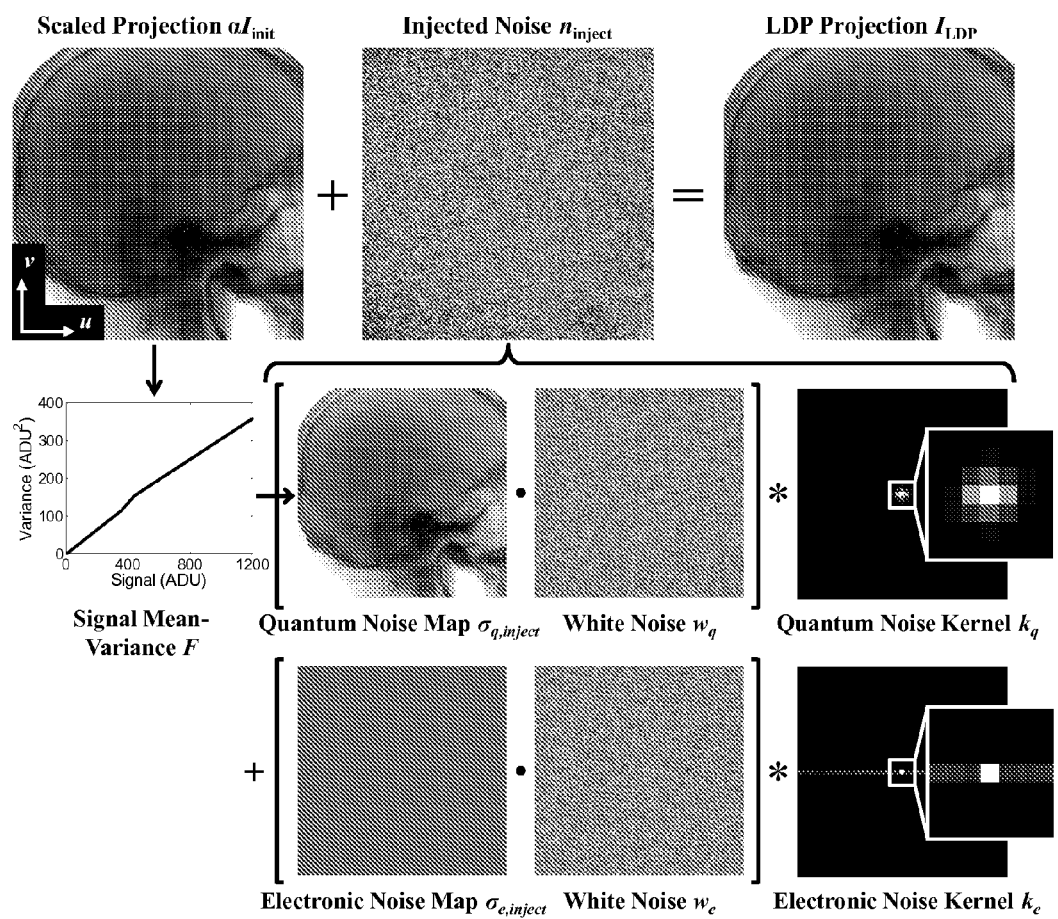
FIG. 2 illustrates an exemplary flowchart of the process for simulating low-dose projections according to an embodiment of the invention.

Referring now to FIG. 2, an exemplary flowchart of the process for simulating low-dose projections according is illustrated according to an embodiment of the invention. The exemplary flow chart illustrates that the scaled projection ($\alpha I_{init}$) plus Injected Noise ($n_{inject}$) provides a low dose projection ($I_{LDP}$). The scaled projection ($\alpha I_{init}$) is based on an initial scan of a patient head and represents a designated amount of x-ray exposure. The noise injected ($n_{inject}$) into the projection data of the scaled projection ($\alpha I_{init}$) accounts for both the magnitude and correlation of both the quantum and electronic noise components at an arbitrary level of dose reduction (fraction $\alpha$) compared to the initial scan. The low dose projection ($I_{LDP}$) represents a projection of a subsequent scan at a lower amount of x-ray exposure than the initial scan.

As to the injection of quantum noise, the variance associated therewith increases approximately linearly with the mean signal. More generally, however, the relationship can be characterized by a function F, where $$\sigma_q^2(u,v) = F(\bar{I})(u,v) \quad (7)$$

and $\bar{I}$ is the mean signal in the projection. In practice, the mean projections are unavailable from a single scan, so the projections of the initial scan $I_{init}$ are used as a surrogate for $\bar{I}_{init}$ (and $\alpha I_{init}$ as a surrogate for $\bar{I}_{LDP}$). The injected quantum variance is then related to the initial projections using the approximation:

$$\sigma_{q,inject}^2(u,v) \approx F(\alpha I_{init})(u,v) - \alpha^2 F(I_{init})(u,v), \quad (8)$$

which generalizes Eq. (5a) to include a potentially non-linear relationship between $\sigma_q^2$ and $\bar{I}$. Since $I_{init}$ is an unbiased (albeit noisy) estimate of $\bar{I}_{init}$ and F is locally well-approximated as a linear transform, the approximation yields an estimate of $\sigma_{q,inject}^2$ that is also unbiased (albeit noisy). The approximation is applied for a high-quality initial scan, and further investigation is needed to verify the ability of a low-dose initial scan to approximate the injected quantum variance and may require using recently developed methods by Zabic et al.[23]

As to the injection of electric noise, a basic model is assumed such that it is spatially invariant and independent of the signal magnitude, with variance $\sigma_e^2$. Therefore, the electronic variance of Eq. (5b) simplifies to:

$$\sigma_{e,inject}^2(u,v) = (1-\alpha^2)\sigma_e^2, \quad (9)$$

which is uniform across the projection.

In addition to the magnitude of the injected noise, the correlations in the noise are an important consideration. Correlations in quantum noise originate primarily from the scintillator blur in (indirect-detection) x-ray imaging devices, while correlations in electronic noise may originate from line noise, crosstalk, etc. in the readout electronics of the detector. The scintillator blur induces noise correlations to the first-order neighborhood of a pixel (resulting in a 3×3 kernel) for the x-ray imaging devices, and the electronic noise possessed a small correlated component along the entire readout line.

These correlations are represented by convolution kernels $k_q$ and $k_e$ for quantum and electronic noise, respectively, which are also assumed to be spatially invariant and independent of exposure. When convolved with white (uncorrelated) noise, these kernels introduce noise correlation to match that found in the projection data. Therefore, while multiplying the standard deviation map $\sigma_{q,inject}$ by white noise $w_q(u, v) \sim N(0, 1)$ i.i.d. (independent and identically distributed) would produce uncorrelated noise of the desired magnitude for injection, the appropriate degree of correlation can be introduced by convolving the resulting product with the kernel $k_q$, as in:

$$n_{q,inject}(u,v) = [(\sigma_{q,inject} \cdot w_q) * k_q](u,v) \quad (10a)$$

where · denotes the Hadamard (element-wise) product and * denotes 2D convolution. Because the standard deviation map $\sigma_{q,inject}(u, v)$ is derived from the initial projection $I_{init}(u, v)$, which includes scintillator blur, the standard deviation map exhibits a degree of unavoidable blur that could contribute to errors in the magnitude of the injected noise $n_{q,inject}(u, v)$; however, the error associated with blur in the noise map is shown to be minor in results reported below. The injected noise exhibits an accurate degree of correlation due to the element-wise product with white noise (which produces spatially uncorrelated noise) followed by convolution with the noise kernel. Note that the kernels $k_q$ and $k_e$ have unit norm so that the magnitude of the injected variance is unchanged even after the correlations are introduced. Similarly, for the electronic noise:

$$n_{e,inject}(u,v) = [(\sigma_{e,inject} \cdot w_e) * k_e](u,v) \quad (10b)$$

with white noise $w_e$ independent of $w_q$. Although the effect of each stage in the imaging chain is not directly modeled (e.g., the conversion of x-rays to optical photons, which typically follows a non-Poisson distribution characterized by the Swank factor), the first- and second-moments of the true distribution in the detected signal can be well-approximated by a Gaussian distribution.[32] While this approximation is expected to break down at very low signal, it is seen to provide a reasonable model over a fairly broad exposure range, as shown below.

Collecting terms, Eq. (1) can be expanded to a closed form for generating LDP projections:

$$I_{LDP}(u,v) = \alpha I_{init}(u,v) + [(\sigma_{q,inject} \cdot w_q) * k_q](u,v) + [(\sigma_{e,inject} \cdot w_e) * k_e](u,v), \quad (11)$$

as illustrated in FIG. 2 for an anthropomorphic head phantom.

The model presented above involves four key characteristics—namely F, σe2, $k_q$, and $k_e$—that can be determined by a calibration measured from projections of a simple phantom. To decouple the quantum and electronic noise contributions of the total noise, projections at two exposure levels are required. For exposure levels $\xi=\{A,B\}$, the noise in a projection is found from the difference of two successive projections in the same position (denoted $I\_(\xi,1)$ and $I\_(\xi,2)$, where 1 and 2 index the two projections with independent noise realizations) and normalized by $\sqrt{2}$:

$$n_\xi(u,v) = (I_{\xi,1}(u,v) - I_{\xi,2}(u,v))/\sqrt{2} \quad (12)$$

The noise kernels are most easily related to the autocorrelation $R_\xi(i,j)$ of the projection noise, which is computed using the definition:

$$R_\xi(i, j) = \frac{1}{N_u N_v} \Sigma_{u,v} n_\xi(u, v) n_\xi(u-i, v-j) \quad (13)$$

$$= \frac{1}{N_u N_v}(n_\xi * n_\xi)$$

where $N_u \times N_v$ is the size of a region-of-interest (ROI) within which the noise is determined, and ★ represents the cross-correlation operation. Note that $R_\xi$ can also be written as the sum of its components:

$$R_\xi(i, j) = R_{q,\xi}(i, j) + R_e(i, j) \quad (14a)$$

$$= \eta m_\xi \tilde{R}_q(i, j) + R_e(i, j) \quad (14b)$$

where $R_{q,\xi}$ and $R_e$ represent the quantum and electronic noise contributions to the autocorrelation, respectively, and $m_\xi$ is the mean value of $I_\xi$ in the ROI. We assume that $R_{q,\xi}$ increases in proportion to exposure and is characterized by a constant slope η (which is in fact the slope of F when F is modeled by a linear relationship), while $R_e$ is independent of exposure. The tilde denotes an autocorrelation function normalized by the variance, such as:

$$\tilde{R}_q(i,j) = R_{q,\xi}(i,j)/R_{q,\xi}(0,0) \quad (15)$$

After computing $R_\xi$ for both exposure levels, $\tilde{R}_q$ and $R_e$ can be solved through a set of linear equations. For example, $R_e$ is solved by extrapolating the exposure to zero, using:

$$R_e(i, j) = \frac{m_B R_A(i, j) - m_A R_B(i, j)}{m_B - m_A} \quad (16)$$

While in some systems $R_e$ could be measured directly from dark-field projections (detector readout in the absence of x-ray exposure), the projections would be zero-mean with electronic noise producing an equal number of positive and negative analog-to-digital units (ADU). In the system used in experiments below, all values were clipped at 0 ADU by the manufacturer (presumably so that an unsigned 16-bit integer data format could be used), so the electronic noise could not be accurately characterized without a positive mean signal to ensure recorded values above 0 ADU—hence the use of two non-zero exposure levels and extrapolation to zero exposure.

The autocorrelation functions can then be related to the convolution kernels. Once $\tilde{R}_q$ (and $\tilde{R}_e$) are determined by the calibration, the corresponding kernels $k_q$ (and $k_e$) can be estimated such that they satisfy:

$$\tilde{R}_q(i,j) = (k_q \star k_q)(i,j) \quad (17)$$

In the results below, the kernels were determined by using the fminunc function in Matlab (MathWorks, Natick, Mass.) to minimize the mean squared error between $\tilde{R}_q$ and $k_q \star k_q$ as follows:

$$\hat{k}_q = \underset{k_q}{\operatorname{argmin}} \left\| \tilde{R}_q - (k_q * k_q) \right\|_2^2 \quad (18)$$

where each $k_q(i,j)$ was a free parameter within a small region about $i=j=0$ that depended on the spatial extent of $R_q$ and was set to 0 elsewhere to better condition the estimation. Alternatively, Fourier methods for estimating and applying the noise kernels could be considered but must be careful to keep the simulated noise real-valued. As noted above, to preserve the magnitude of the variance while introducing the correlations, the norm of $k_q$ (and $k_e$) must equal 1, which is satisfied since:

$$\Sigma_{u,v} k_q^2(u,v) = \tilde{R}_q(0,0) = 1 \quad (19)$$

The electronic variance is given by $\sigma_e^1 = R_e(0, 0)$, and the signal mean-variance relationship F can be determined by first sorting and binning the values in the average projection $\bar{I}_\xi = (I_{\xi,1} + I_{\xi,2})/2$. The variance of $n_\xi$ for the pixels in each bin was plotted against the mean $\bar{I}_\xi$ for the pixels in each bin, after subtracting the electronic noise variance $\sigma_e^2$ so that only the quantum variance remains. A linear fit approximating F can then be applied to the sample points derived from the binned data.

Referring again to FIG. 1, at step 105, at least one low-dose preview image is displayed, by at least one processor, based on said reconstruction of the at least one initial image projection according to an algorithm specific to a task of the patient and based on the detected signal and the injection of said correlated noise. Preferably, a plurality of low-dose preview images are displayed which are injected with varying amounts of correlated noise. Further, each of the plurality of low-preview images may represent at least one of a variation of detector blur and a variation of detector gain. The low-dose preview image is a preview of at least one of a radiographic image, a fluoroscopic image, a tomosynthesis reconstruction, a computed tomography reconstruction and a cone-beam computed tomography reconstruction. In a particular embodiment of the current invention, each of the plurality of low-dose preview images may be a different type of low-dose preview image. For example, whereas one low-dose preview image may be of a radiographic image, another low-dose preview image may be of a fluoroscopic image.

When the at least one low-dose preview image is displayed, the user has the option of performing a new reconstruction of the at least one initial image projection according to an algorithm specific to a task of the patient and based on the detected signal. The new reconstruction may be based on an injection of a different amount of correlated noised into the at least one initial image projection of the initial scan of the patient, therefore providing a view of different amounts of x-ray exposure than the previously reconstruction.

Thereafter, at step 106, upon displaying the at least one low-dose preview image, a selection of the at least one low-dose preview image is enabled by at least one processor based on said at least one initial image projection according to an algorithm specific to a task of said patient and based on said detected signal and said injecting of said correlated noise for at least one subsequent scan.

Another embodiment includes the introduction of virtual insertion of interventional devices, since such devices (e.g., a deep-brain stimulation electrode or transpedicle spine screws) may be introduced during a procedure and result in degraded image quality. The LDP could therefore allow the user to anticipate the change in image quality arising from the device (e.g., photon starvation) and select the optimal protocol based on images with realistic artifact and noise. One possible approach would be to allow the user to virtually place the interventional device in its anticipated location in the image, followed by forward-projecting the device and modifying the projections so that the affected rays are attenuated and increased in noise.

The LDP may be used in surgery where the timescale between CBCT acquisitions at specific milestones in the operation may range from ~10-60 minutes (depending on the procedure and workflow), and in IGRT timescales of 1 day between fractions would allow for a potentially large menu of LDP images to be computed at various levels of dose reduction, reconstruction techniques, and reconstruction parameters. The use of LDP may be integrated into such workflow to avoid excess manual intervention and prevent user error. For example, the image menu could be constrained to a fixed number of images within a predetermined dose range that avoids unreasonably low dose protocols while still encouraging dose reduction. The patient-specific LDP images would then enable a number of new capabilities in prospective dose reduction—including task-specific and observer-specific selection of minimum-dose protocols.

Additionally, the use of LDP would be equally valuable for setting general guidelines (e.g., CBCT technique charts) based on attributes such as patient size and imaging task, as well as for training purposes for new users of CBCT systems. Therefore, the LDP method can be a powerful tool to both prospective and retrospective approaches by providing accurate visualization of the impact of low-dose protocols and (advanced) reconstruction methods on CBCT image quality.

I. EXAMPLES

A. Introduction

The proposed LDP method was experimentally tested using a prototype mobile C-arm (modified Powermobil, Siemens Healthcare, Erlangen, Germany; see FIG. 1) capable of CBCT. A computer-controlled motorized drive provided continuous rotation of the C-arm over a ~178° orbit while collecting 198 projections, and the source-axis distance (SAD) of 60 cm and source-detector distance (SDD) of 120 cm provided a ~15×15×15 cm³ volumetric field of view (FOV). A previously developed geometric calibration phantom was used to measure the source-detector position of each projection relative to the C-arm isocenter, which was represented as projection matrices.[33-35] The x-ray source was operated in pulsed-fluoroscopic mode, with the tube potential fixed at 100 kVp while the tube output of the scan was varied from 20-320 mAs in the head and 30-480 mAs in the body.

The C-arm was equipped with a Varian PaxScan 3030+ FPD (Varian Medical Systems, Palo Alto, Calif.) operated by the system manufacturer in 2×2 binning mode (768×768 effective pixels at 388 µm pitch) and in dual-gain mode to increase the signal dynamic range. For each projection, a high-gain image was recorded to provide a larger dynamic range for low signal values, while a low-gain image was recorded to prevent saturation of high signal values. The dual-gain measurements were then corrected for detector dark current offset and combined into a 16-bit unsigned integer ADU value per pixel, with a minimum signal value of zero enforced. These corrected and combined projections were the input to the LDP calibration and validation. Due to the different gains, the signal-variance relationship F was composed of two distinct regions as seen in FIG. 2—a low-signal, high-gain region and a high-signal, low-gain region. Based on the empirical measurements of F, it was found that the low-signal region ranged from [0, 360] ADU, while the high-signal region ranged from [440, $2^{16}-1$] ADU. Therefore, in approximating F with a linear relationship, separate linear fits were applied to the two regions. A linear interpolation was applied between the fitted values at 360 and 440 ADU to provide a piecewise-linear fit to F that ensures continuity and an increasing relationship.

Radiation dose was previously measured and reported in the head and body, using a 0.6 cm Farmer ionization chamber (Accu-Pro, RadCal, Monrovia, Calif.). The head dose was measured in an acrylic 16 cm diameter cylindrical CTDI phantom, and good linearity was observed between specified tube output (mAs) and measured dose, with a conversion of 0.041 mGy/mAs at 100 kVp. The dose in the abdomen was measured in an oblate abdominal phantom (QRM GmbH, Erlangen, Germany) and found to be 0.026 mGy/mAs at 100 kVp.

1. Calibration and Assessment of LDP in Head Imaging

The accuracy of the LDP method was first evaluated for head imaging. Calibration measurements for F, $\sigma_e$, $k_q$, and $k_e$ were obtained with the 16 cm acrylic cylinder wrapped in an 8 mm thick PVC layer (simulating the skull) scanned twice each at settings of 100 kVp, {20, 40, 80, 160, and 320} mAs.

Following calibration, quantitative analysis of LDP accuracy was performed in an anthropomorphic head phantom comprising a human skull encased in Rando tissue-equivalent plastic with seven 12.7 mm diameter plastic spheres embedded within the interior of the cranium with contrast ranging from ~40 to 900 HU (The Phantom Laboratory, Greenwich, N.Y.; see FIG. 1). The head phantom was scanned twice, each at the same techniques as the calibration phantom. The 320 mAs technique was used as the "initial" CBCT, and LDP projections were formed at 20, 40, 80, and 160 mAs. The reconstructed LDP images were then compared with real images at the same techniques. As detailed below, the two sets of scans (and preview images) at each technique allowed determination of image noise from the difference images of two i.i.d. realizations.

2. Calibration and Assessment of LDP in Body Imaging

Since body imaging involves increased attenuation and scatter compared to head imaging (with possible effects on F and $k_q$), a separate calibration was performed for body imaging using the oblate abdominal QRM phantom. A second oblate thoracic phantom (QRM GmbH, Erlangen, Germany) was placed immediately superior to the abdomen phantom, and an acrylic 32 cm CTDI body phantom was placed immediately inferior to provide fairly realistic scatter from outside the imaging volume. The imaging techniques were 100 kVp, {30, 60, 120, 240, and 480} mAs, each acquired twice.

After calibration with the abdominal phantom, studies were conducted using a fresh, unfixed cadaveric torso presenting realistic bone, soft-tissue structures, and fine-detail gas pockets in the bowel. The same imaging techniques as the body calibration were acquired for the cadaver, with the 480 mAs scan used as the "initial" CBCT, and the remaining scans used for comparison between LDP and real images.

B. Image Reconstruction

In addition to conventional filtered backprojection (FBP) reconstruction, the penalized-likelihood (PL) framework may be applied as a representative selection of the much broader class of MBIR algorithms such as total-variation (TV) minimization, penalized weighted least-squares, compressed sensing, and tight-frame regularization. The LDP and real CBCT projections were both reconstructed using FBP and PL. While both FBP and PL offer reconstruction parameters that may be freely tuned (for example, trading off spatial resolution and image noise), for simplicity only one set of parameters was selected that was representative of each reconstruction algorithm.

All images were reconstructed with isotropic 0.6×0.6×0.6 mm³ voxels using Matlab, which interfaced with custom external libraries for the computationally intensive 3D forward and backprojectors. The projectors were implemented in CUDA for GPU acceleration (GTX 680, nVidia, Santa Clara, Calif.) and utilized the separable footprints with trapezoid functions (SF-TT) method for projecting voxels onto the detector plane. While other projection methods could have been used, SF-TT was shown by Long et al to be more accurate than other methods, such as the distance-driven method or Siddon's method.

1. Cone-Beam Filter Backprojection (FBP)

Cone-beam FBP reconstruction was performed with a modified Feldkamp-Davis-Kress (FDK) algorithm applied to the line integrals $l=-\log(I/I_0)$, where I is a projection (preview or real) and $I_0$ is the flood-field projection.[46] A minimum value of $I=I_0 e^{-8}$ was enforced (i.e., the line integrals were capped at 8, corresponding to ~40 cm water taken as a reasonable estimate of object diameter for the abdomen) to avoid streak artifacts from photon starvation. Although clipping the values like this may introduce a bias in the line integrals, the method was applied to both the preview and real projections, which provided a consistent comparison between the two. The lateral edge values were extended beyond the detector edge (in the u-direction) as a form of basic truncation correction, and a Hann window with cutoff frequency $f_c=0.4\times f_{Nyquist}$ was applied to the ramp filter. No scatter or beam-hardening corrections were applied to either the preview or real reconstructions, although the LDP process is compatible with various artifact correction or post-processing methods that might be applied, since it uses the projection data directly.

2. Penalized Likelihood (PL) Iterative Reconstruction

The penalized likelihood method combines a data consistency term with image regularization to form the reconstructed image. The data consistency term utilizes a statistical model of the projections I to construct the log-likelihood function $L(\mu; I)$ for image $\mu$, while image regularization penalizes the image roughness $R(\mu)$ with strength $\beta$. The reconstructed image is then the solution $\hat{\mu}$ to the following optimization problem:

$$\hat{\mu} = \arg\max_{\mu} L(\mu; I) - \beta R(\mu) \tag{20}$$

which seeks to maximize the likelihood function while penalizing image roughness (e.g., noise). In order to apply a statistical model to the data, the projection measurements I and flood-field air scan $I_0$ were first normalized by the effective detector gain $\eta_0$, so that $$\tilde{I} = I/\eta_0, \tag{21}$$

$$\tilde{I}_0 = I_0/\eta_0,$$

where $$\eta_0 = \mathrm{Var}(I_0)/E[I_0] \tag{22}$$

Then a basic Poisson statistical model was applied, with $$\tilde{I} \sim \mathrm{Poisson}(\tilde{I}_0 \exp(-A\mu)) \tag{23}$$

where A is the forward-projection operator. Although it has been shown that the true statistics are neither independent (due to spatial correlations) nor Poisson distributed (due to the various detector gain stages and additive electronic noise), this model provides a basic form of statistical weighting of the measurements that is commonly applied in practice. The log-likelihood function (ignoring constant terms) is then $$L(\mu;I) \cong -\Sigma_i [\tilde{I}_0 \exp(-A\mu)]_i + \tilde{I}_i [A\mu]_i \tag{24}$$

The image regularization reduces image noise in a manner that generally trades off spatial resolution with image noise (though in a different manner than FBP). Regularization was applied to a first-order neighborhood N of each voxel, with unity weights $w_{jk}$ and penalty function $\psi$ applied to the difference of neighboring voxels:

$$R(\mu) = \Sigma_j \Sigma_{k \in N} w_{jk} \psi(\mu_j - \mu_k) \quad (25)$$

Rather than a basic quadratic penalty function $\psi_Q(x) = 1/2x^2$, an edge-preserving penalty is often adopted to provide lower noise images while maintaining edge information. In results reported below, the Huber penalty function $$\psi_H(x) = \begin{cases} \frac{1}{2\delta} x^2, & |x| \le \delta \\ |x| - \frac{\delta}{2}, & |x| > \delta \end{cases} \quad (26)$$

was used, which provides a greater degree of edge-preservation for smaller $\delta$ at the potential expense of blotchy image texture.

The PL reconstructions were initialized by the corresponding FBP reconstructions and iteratively solved with the ordered subset, separable quadratic surrogates (OS-SQS) technique, which allowed for all voxels to be updated simultaneously per iteration.[47, 48] The primary computational burden lay with the forward- and back-projection operations per iteration, which were accelerated by GPU implementation of the projectors. The OS-SQS algorithm was run for 200 iterations with 11 subsets, and the selected PL reconstruction parameters were $\delta = 10^{-3}$ mm$^{-1}$ and $\beta$ numerically equivalent to the tube output (e.g., $\beta = 20$ for the 20 mAs scan), which coincidentally served as a convenient selection of $\beta$ (as opposed to a formal relationship) that also took into account the need for larger $\beta$ with higher $I_0$. These values of $\delta$ and $\beta$ served as a fairly general-purpose selection that avoided patchy image noise and preserved spatial resolution. Alternative parameter selection—for example, specifically to enhance soft-tissue imaging performance[37]— is possible and completely compatible the LDP process.

C. Assessment of Image Quality and Accuracy of LDP Images

The accuracy of the LDP was quantitatively assessed by comparison of spatial resolution, image contrast, and image noise characteristics of the LDP and real low-dose images. Since neither the injection of noise (for the LDP images) nor the reduction of exposure (for the real images) was expected to affect the spatial resolution or absolute contrast, these two metrics provided a "sanity check" to ensure that the LDP algorithm did not have unexpected adverse effects on image quality, and emphasis of the analysis was on the accuracy of the LDP image noise magnitude and correlation.

1. Spatial Resolution

The spatial resolution was assessed by measuring the edge spread function (ESF) of the high-contrast sphere (3 o'clock position, FIG. 1) in the anthropomorphic head phantom. The sphere was divided into twelve non-overlapping 30° conical sections whose apices were at the center of the sphere and axes lay in the axial plane, and an error function (erf) was fit to the edge. The derivative of the erf (a Gaussian) yielded the line spread function (LSF) characterized by its full-width at half-maximum (FWHM). The difference in measured FWHM between the LDP and real CBCT images for all twelve conical sections and for both realizations at each dose level provided 24 measurements for evaluating the preservation of spatial resolution.

2. Image Contrast

The seven spheres embedded in the anthropomorphic head phantom provided varying contrast levels (ranging from ~40 to 900 HU) that were compared between the preview and real images. For each reconstructed image, the contrast of each sphere was determined by subtracting the average attenuation within the sphere (20 voxel diameter ROI) from the average attenuation adjacent to the sphere (also a 20 voxel diameter ROI). Agreement was assessed by examining the difference in contrast between the LDP and real images for all seven spheres and in both realizations at each dose level. Although the images were reconstructed with units of mm$^{-1}$, the image contrast (and noise) were converted to HU by an approximate factor of $5 \times 10^4$ HU/mm$^{-1}$ determined from CBCT images of known materials (e.g., water) in comparable head and body phantom configurations.

3. Image Noise

Since CBCT images were acquired twice at each dose level, subtraction of two reconstructions at each tube output level was used to measure image noise (after normalization by $\sqrt{2}$). The noise magnitude was first assessed by measuring the standard deviation within an ROI. In the anthropomorphic head phantom, the standard deviation was measured in a 51×51 voxel ROI at the center of the axial plane for the 31 central slices and averaged. In the cadaveric torso, the standard deviation was measured in a 51×51 voxel ROI centered on the right kidney (i.e., within a reasonably homogeneous region of soft-tissue) in the coronal plane and averaged across 31 coronal slices centered on the kidney.

Accurate reproduction of noise texture in the reconstructed LDP images was also assessed by computing the noise-power spectrum (NPS).[49-51] Both axial-plane and longitudinal (z-) direction NPS were considered, since detector correlations were expected to affect both. In the head phantom, the 2D NPS was computed in the axial plane and averaged in the longitudinal direction for the 51×51 voxel ROIs in the 31 axial slices at the center of the volume. A radial average of the 2D NPS was performed to reduce statistical error in the NPS estimate. In the cadaver, the 1D NPS was computed in the longitudinal (z-) direction and averaged in the other directions for the 51×51 voxel ROIs in the 31 coronal slices centered on the kidney. It was assumed that within these small ROIs, the properties were locally stationary such that the computed NPS were representative of the local noise texture. Additionally, the ROIs avoided high-contrast edges so as to avoid the non-linear behavior of the PL edge-preserving penalty.

Finally, as a basis of comparison to naïve simulation of noise without proper accounting of correlation, LDP projections were created by injecting white noise rather than correlated noise (i.e., using $k_q = k_e = \delta_2$, a 2D discrete impulse function). The injected noise therefore possessed the correct magnitude but was not spatially correlated. The resulting LDP images were similarly assessed in terms of the NPS, hypothesizing that the reconstructed image NPS would be lower when injecting white noise due to the effect of the reconstruction process.

D. Calibration Phantom Empirical Results

1. Signal-Variance Mapping

Figure 3:
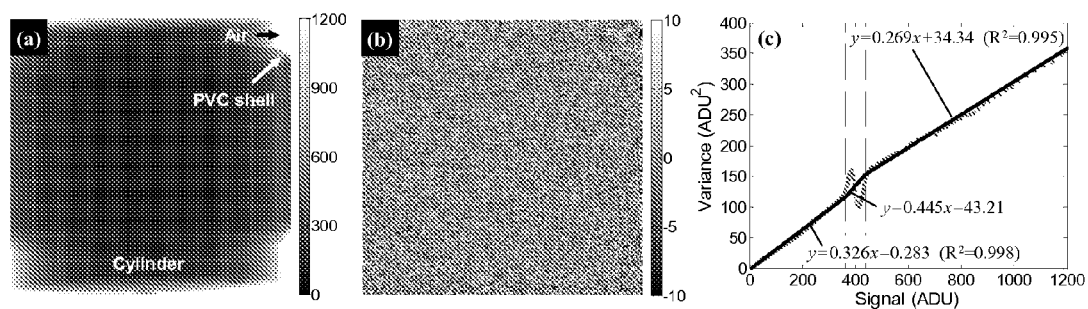
FIG. 3 illustrates an exemplary calibration of a signal-variance relationship according to an embodiment of the invention.

FIG. 3 illustrates an exemplary calibration of a signal-variance relationship according to an embodiment of the invention Section (a) of FIG. 3 illustrates a single projection of the 16 cm acrylic cylinder from the 1.6 mGy (100 kVp, 40 mAs) acquisition, with grayscale pixel values in ADU. Section (b) of FIG. 3 illustrates a noise realization computed from the difference image of two projections (normalized by √2), displayed in ADU. Section C of FIG. 3 illustrates a signal mean-variance relationship for a head-sized object and the 1.6 mGy technique. The points represent the measurements, and the lines represent linear fits in the high-gain [0, 360] ADU and low-gain [440, $2^{16}-1$] regions, with a linear interpolation in the transition region between [360, 440] ADU. Two linear regions can be observed for this FPD (which employs a dual-gain readout mode)—a high-gain region from 0 to ~360 ADU and a low-gain region above ~440 ADU. Within each region, a linear fit described the signal-variance relationship well ($R^2>0.99$). A seemingly non-monotonic relationship was observed in the transition between the two regions. The transition region corresponds to signal overlap between the two gain modes, and the behavior of the variance-signal relationship here could be due to a slightly suboptimal combination (from a noise perspective) of dual-gain readout by the system manufacturer. Because the observed effect covered only a small fraction of the detector dynamic range, for simplicity, the transition region was approximated by a linear interpolation between the low-gain and high-gain linear fits that might be better generalized to other detectors, and the mismatch in projection variance within this narrow region was expected to have a small effect overall. The y-intercept is near 0, since the measured electronic variance $\sigma_e^2=4.47$ ADU$^2$ was subtracted out prior to fitting.

2. Noise Cancellation Kernels

Figure 4:
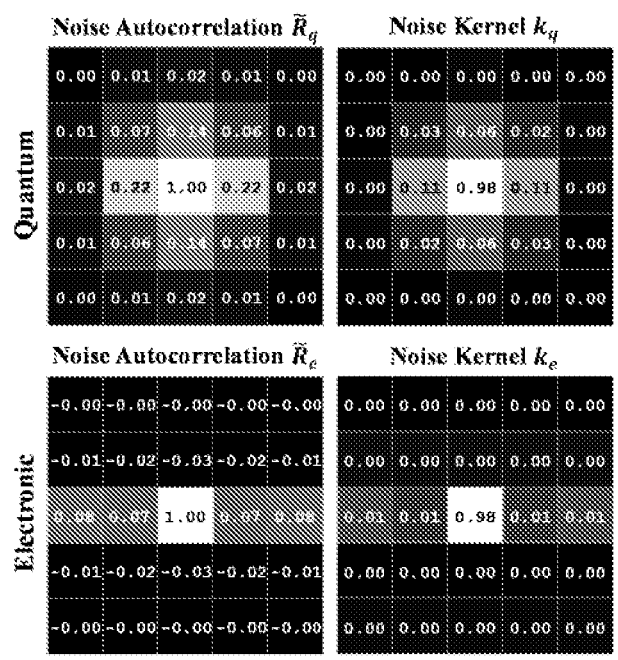
FIG. 4 illustrates an exemplary central region of the measured noise autocorrelation $\tilde{R}_q$ and $\tilde{R}_e$ from a calibration phantom according to an embodiment of the invention.

Noise autocorrelation functions were computed as in Eq. (13) using projections of the calibration phantom from the 100 kVp, 20 and 40 mAs scans. As illustrated in FIG. 4, the major portion of quantum noise correlation was contained within the central 5×5 region of $\tilde{R}_q$, with an autocorrelation coefficient of up to 0.22 for neighboring pixels and falling to zero outside the central 5×5 region. A slight asymmetry in the u- and v-directions was observed, with stronger correlations in the u-direction. Although commonly assumed to be uncorrelated, $R_e$ was found to exhibit correlation across v=0, the direction of detector readout lines, with an autocorrelation coefficient of up to 0.08 for pixels along the same readout line.

Due to the generally ill-conditioned nature of estimating $k_q$ as a free parameter consistent with $\tilde{R}_q$ as in Eq. (18), only the central 3×3 region of $k_q$ was allowed to vary, with a value of 0 enforced elsewhere. For estimating $k_e$, only the elements along v=0 were allowed to vary from zero, which captured most of the correlated behavior of electronic noise. More advanced models for estimating $k_e$ could also account for the small amounts of negative correlation observed along v=±1. The resulting noise kernels (FIG. 4) were used in the LDP of the anthropomorphic head phantom.

E. Anthropomorphic Head Phantom Results

Figure 5:
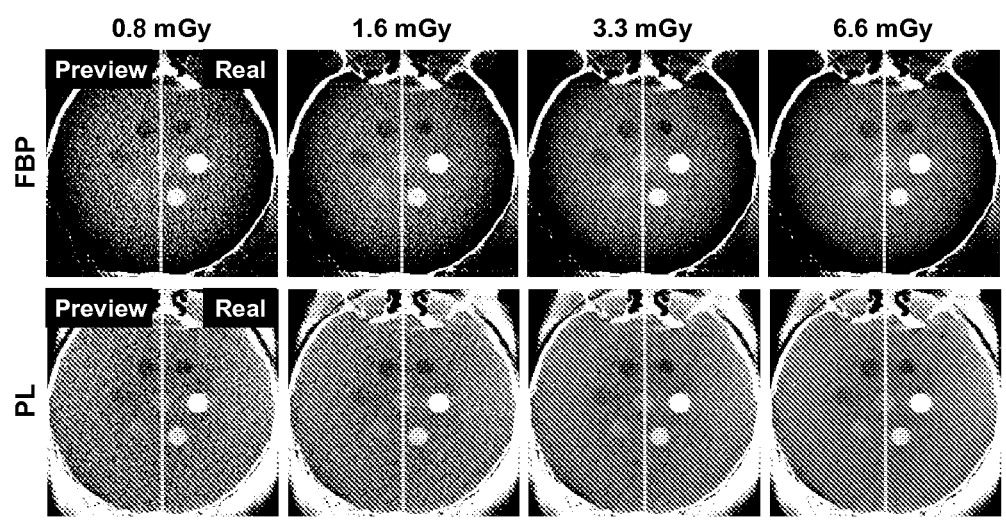
FIG. 5 illustrates an exemplary side-by-side split comparison between LDP and real CBCT images acquired at dose reduced from that of the initial image according to an embodiment of the invention.

FIG. 5 illustrates an exemplary side-by-side split comparison between LDP and real CBCT images acquired at dose reduced from that of the initial image according to an embodiment of the invention. In each case, the left half shows the LDP, and the right half is a real CBCT acquired at the stated low-dose technique. The top row of FIG. 5 illustrates FBP reconstructions and the bottom row of FIG. 5 illustrates Fig PL reconstructions. The image quality and noise characteristics demonstrate qualitative agreement, with LDP images realistically depicting the increase in noise at lower dose and a distinct difference in noise texture observed between reconstruction methods. Images are displayed on a [0.015, 0.023] mm$^{-1}$ grayscale window.

The LDP reconstructions shown in FIG. 5 are computed from an initial CBCT acquired at 320 mAs (13.1 mGy). In each case, the LDP image is shown split side-by-side with a real CBCT image acquired at the reduced-dose technique (20, 40, 80, and 160 mAs, corresponding to 0.8, 1.6, 3.3, and 6.6 mGy, respectively). The LDP and real images agree qualitatively, demonstrating realistic image quality, including the increased noise at lower dose and the effect of reconstruction algorithm (FBP or PL). For example, FBP has streak artifacts from the incomplete orbit and reduced image intensity at the edge of the circular FOV, while PL mitigates these artifacts. Additionally, with the selected PL parameters, the PL images exhibit lower noise and visibly different noise texture than the corresponding FBP images. Such characteristics are readily appreciated in viewing the LDP images and could be difficult to appreciate otherwise, illustrating how the LDP process could guide low-dose protocol selection in a manner that includes nonlinear artifacts and complex characteristics of the reconstruction method.

Figure 6:
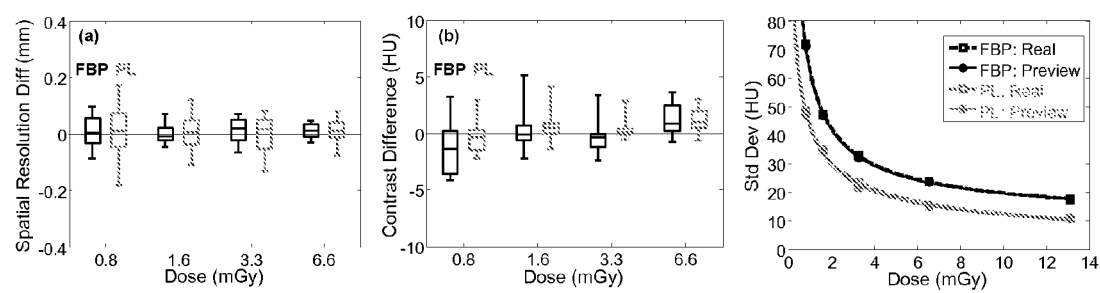
FIG. 6 illustrates an exemplary quantitative comparison between LDP and real CBCT images for FBP (black) and PL (gray) reconstructions across all dose levels according to an embodiment of the invention.

FIG. 6 illustrates an exmplary quantitative comparison between LDP and real CBCT images for FBP (black) and PL (gray) reconstructions across all dose levels according to an embodiment of the invention. Section (a) of FIG. 6 illustrates the difference in measured spatial resolution (mm). Section (a) of FIG. 6 illustrates the difference in measured contrast (HU) of spheres in the head phantom. Section (a) of FIG. 6 compares the measured image noise (HU). Each metric demonstrates strong agreement between LDP and real CBCT images.

Moreover, Section (a) of FIG. 6 illustrates the difference in spatial resolution (mm) measured between the LDP and real CBCT images showed an agreement within 10±37 µm (mean±std) for FBP and 9±62 µm for PL across all dose levels. Additionally, section (b) of FIG. 6 shows that the image contrast is in agreement within −0.09±2.00 HU for FBP and 0.50±1.28 HU for PL across all dose levels. These findings demonstrate that the LDP process of scaling projections and injecting noise does not alter the spatial resolution or image contrast, as expected. On the other hand, the image noise increases at lower dose as shown in FIG. 6 (c), showing agreement within 2.9% for FBP and 6.4% for PL. A power-law curve fit ($y=ax^b+c$) was applied to the measured noise at the five dose levels and plotted up to the 13.1 mGy dose of the initial CBCT. The LDP and real CBCT curve fits overlap almost identically, with PL presenting lower noise than FBP for this particular set of reconstruction parameters (which are not meant to serve as a direct comparison between PL and FBP).

Figure 7:
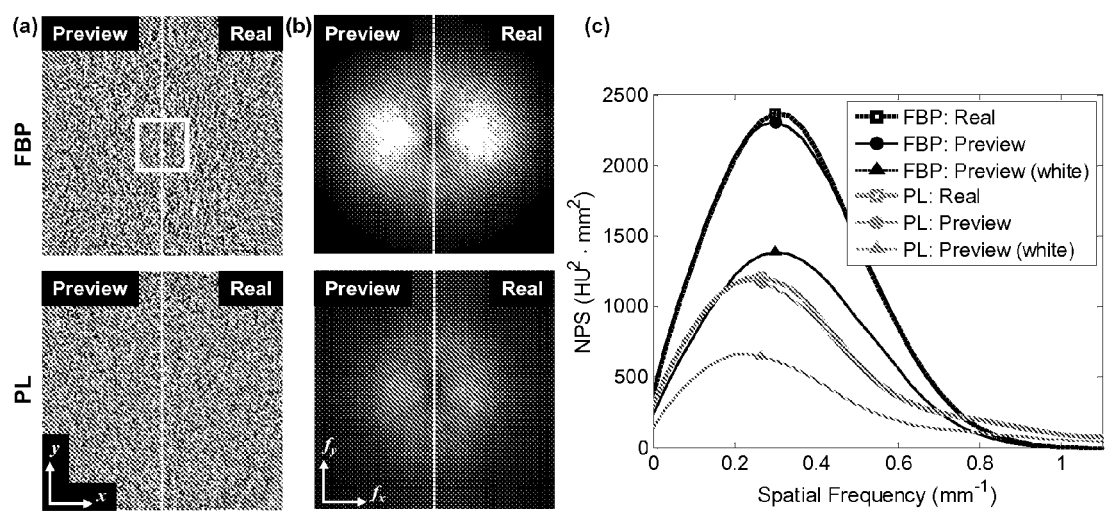
FIG. 7 illustrates an exemplary comparison of reconstructed image NPS measured in LDP and real CBCT images at 1.6 mGy according to an embodiment of the invention.

FIG. 7 illustrates an exemplary comparison of reconstructed image NPS measured in LDP and real CBCT images at 1.6 mGy according to an embodiment of the invention. Section (a) of FIG. 7 illustrates a difference image in the axial plane for (top) FBP and (bottom) PL reconstructions, showing qualitatively good agreement in the magnitude and noise between LDP and real images. The white square in section (a) of FIG. 7 marks the position of the 3D ROI for computing the local NPS. Display window [−80, 80] HU. Section (b) of FIG. 7 illustrates an axial NPS shown in split side-by-side comparison of LDP and real CBCT. Display window [0, 3200] HU$^2$ mm$^2$. Section (b) of FIG. 7 illustrates a radially averaged axial NPS. The NPS of LDP and real CBCT images are in close agreement, whereas preview images simulated using a naive injection of white noise underestimates the NPS by almost a factor of 2.

The local NPS of 3D image reconstructions demonstrate strong agreement when detector correlations are correctly modeled, as shown in FIG. 7 for the 1.6 mGy case. The noise exhibits similar levels of magnitude and texture between the LDP and real CBCT images and illustrates the difference in noise characteristics between the FBP and PL reconstructions. The 2D axial NPS side-by-side split-comparison exhibits the expected Hermitian symmetry, while again illustrating the difference in noise magnitude and texture between FBP and PL reconstructions. The enhanced lobes along the $f_x$-axis result from the asymmetry of the object (i.e., the head phantom exhibits a larger path length in the anterior-posterior (y-) direction).

Section (c) of FIG. 7 illustrates a radially-averaged NPS plot demonstrating a strong agreement between the LDP and real CBCT noise, with the NPS for LDP peaking at a slightly lower value by 2.5% for FBP and 3.1% for PL. However, preview images simulated with a naïve white noise injection exhibit substantially lower noise-power and do not realistically portray the image noise at reduced dose. The peak of the NPS with naive white noise injection is lower by 41.5% for FBP and 46.5% for PL, and the shape of the curve (and therefore, the noise texture) also differs from the real image NPS. While the injected white noise contains an equal amount of noise-power at all frequencies, the injected correlated noise was formed by convolution with noise kernels that boosts the noise-power at lower frequencies (particularly $k_q$, which has a low-pass characteristic typical of an indirect-detection FPD) while reducing the injected noise power at higher frequencies in a manner that conserves the injected noise magnitude (since $\|k_g\|=\|k_e\|=1$). Because image reconstruction effectively acts as a bandpass filter in the axial plane (i.e., ramp filter with Hann window and backprojection in FBP, or image regularization in PL), the boosted lower-frequency noise-power of the injected correlated noise is evident by the higher main lobe of the reconstructed image NPS.

F. Cadaver Abdomen

Figure 8:
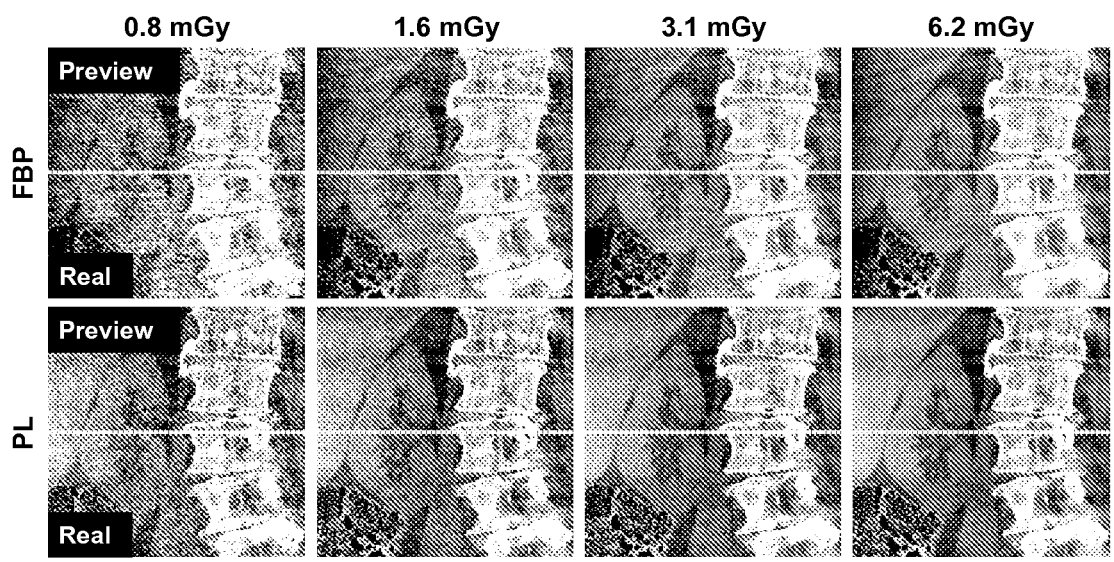
FIG. 8 illustrates an exemplary comparison of LDP and real CBCT images in a coronal slice of the cadaveric torso according to an embodiment of the invention.

FIG. 8 illustrates an exemplary comparison of LDP and real CBCT images in a coronal slice of the cadaveric torso according to an embodiment of the invention. The top half of each image is from the LDP, and the bottom half is from a real CBCT acquisition at each technique. The differences in image quality in (Top row) FBP and (Bottom row) PL reconstructions at different dose levels is well-depicted by LDP. Display window [0.016, 0.022] $mm^{-1}$.

The split comparison shows qualitatively good agreement between the LDP and real CBCT images in features such as the fine-detail, high-contrast vertebrae, the contrast of soft-tissue structures, and the increase in image noise at lower dose. The LDP images could enable a clinician to confidently select a patient-specific, minimum-dose protocol in a manner that directly considers the imaging task (as well as the observer's preferences)—for example, in selecting a protocol sufficient for high-contrast bone detail, PL at 0.8 mGy. Numerous other considerations could (and should) be incorporated in technique selection as well—e.g., although PL improves overall image quality, FBP may be preferred for reasons of speed in fast, repeat scans sufficient for high-contrast visualization. On the other hand, for visualization of the kidney, liver, muscle, and surrounding fat, LDP would enable the user to determine a minimum-dose technique and reconstruction algorithm sufficient for imaging of low-contrast soft tissues—e.g., PL at 3.1 mGy.

Figure 9:
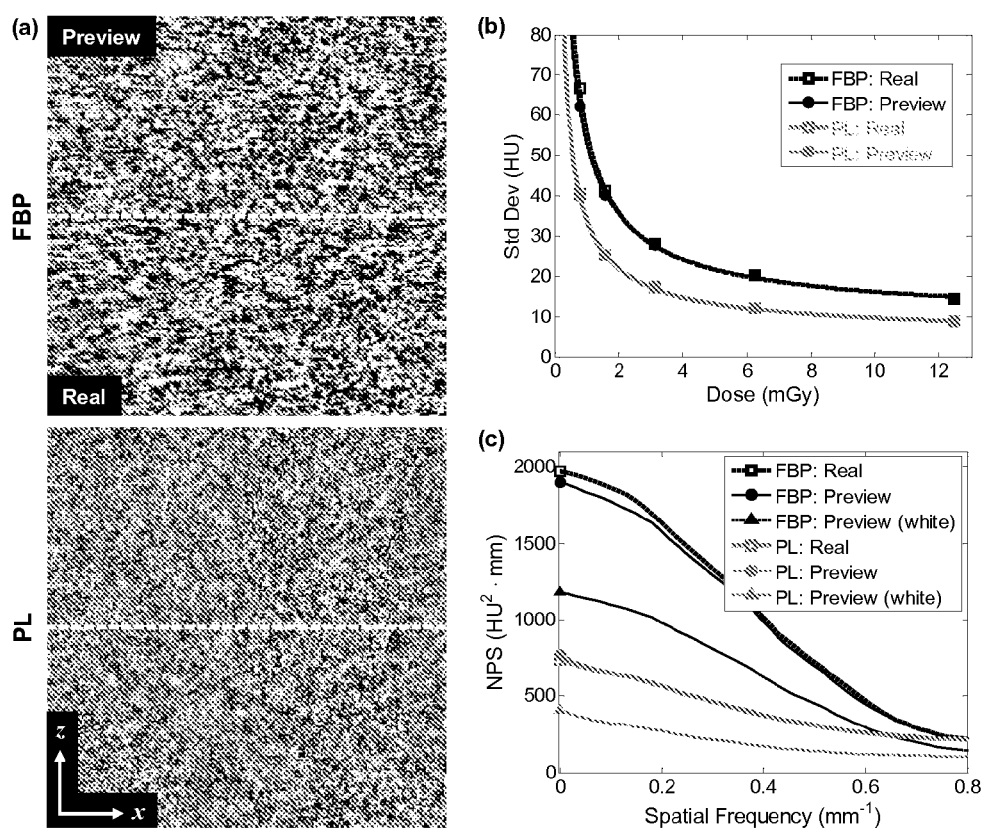
FIG. 9 illustrates an exemplary comparison of LDP and real CBCT image noise in the torso cadaver according to an embodiment of the invention.

Referring now to FIG. 9, an exemplary comparison of LDP and real CBCT image noise in the torso cadaver is illustrated according to an embodiment of the invention. Section (a) of FIG. 9 illustrates a difference image (coronal slice, 1.6 mGy, display window [−50, 50] HU). Section (b) of FIG. 9 illustrates image noise evaluated in a ROI in the kidney as a function of dose. Section (c) of FIG. 9 illustrates longitudinal NPS (1.6 mGy) shows close agreement in the LDP and real CBCT noise, whereas a naive white noise injection underestimates the NPS.

More specifically, section (a) of FIG. 9 illustrates that the difference images (coronal slices) in 3D reconstructions of the cadaver images at 1.6 mGy show the noise to be strongly correlated and non-stationary. For example, PL exhibits noise that is highly dependent on the object, and edge-preservation of high contrast structures such as bone-tissue or air-tissue interfaces causes larger differences at these edges in the difference image. The ROI in the soft tissue (kidney) therefore provides more homogeneous noise characteristics for standard deviation and NPS analysis. The agreement in standard deviation between LDP and real CBCT images was within 6.7% for FBP and 1.1% for PL across all dose levels [section (b) of FIG. 9]. For the longitudinal NPS at 1.6 mGy [section (c) of FIG. 9], LDP exhibited peak noise-power at a spatial frequency that was just 3.7% lower for FBP and 4.7% higher for PL, likely within experimental error. On the other hand, simulation of low-dose images with a naive injection of white noise yields NPS peaking at a frequency 40.6% lower for FBP and 44.7% lower for PL and grossly underestimating the total noise magnitude. Here again, the correlations in the quantum noise boost the lower frequencies in the injected noise, and a white noise model leads to inaccurate noise estimates that could cause one to underestimate the effect of low-dose protocols on image noise.

REFERENCES

II. 1. R. Fahrig, A. J. Fox, S. Lownie, and D. W. Holdsworth, "Use of a C-arm system to generate true three-dimensional computed rotational angiograms: preliminary in vitro and in vivo results," American Journal of Neuroradiology 18(8), 1507-1514 (1997).

III. 2. D. A. Jaffray, J. H. Siewerdsen, J. W. Wong, and A. A. Martinez, "Flat-panel cone-beam computed tomography for image-guided radiation therapy," International Journal of Radiation Oncology Biology Physics 53(5), 1337-1349 (2002).

IV. 3. J. H. Siewerdsen et al., "Volume CT with a flat-panel detector on a mobile, isocentric C-arm: Pre-clinical investigation in guidance of minimally invasive surgery," Medical Physics 32(1), 241 (2005).

V. 4. M. J. Daly, J. H. Siewerdsen, D. J. Moseley, D. A. Jaffray, and J. C. Irish, "Intraoperative cone-beam CT for guidance of head and neck surgery: Assessment of dose and image quality using a C-arm prototype," Medical physics 33, 3767 (2006).

VI. 5. G.-H. Chen, "Design and development of C-arm based cone-beam CT for image-guided interventions: initial results," in *Proceedings of SPIE* (SPIE, 2006), pp. 614210-614210-12.

VII. 6. M. J. Wallace, M. D. Kuo, C. Glaiberman, C. A. Binkert, R. C. Orth, and G. Soulez, "Three-dimensional C-arm cone-beam CT: applications in the interventional suite," Journal of Vascular and Interventional Radiology 19(6), 799-813 (2008).

VIII. 7. R. C. Orth, M. J. Wallace, and M. D. Kuo, "C-arm cone-beam CT: general principles and technical considerations for use in interventional radiology," Journal of vascular and interventional radiology: JVIR 19(6), 814-20 (2008).

IX. 8. A. C. Miracle and S. K. Mukherji, "Conebeam CT of the head and neck, part 2: clinical applications," American Journal of Neuroradiology 30(7), 1285-1292 (2009).

X. 9. S. Schafer et al., "Mobile C-arm cone-beam CT for guidance of spine surgery: Image quality, radiation dose, and integration with interventional guidance," Medical physics 38, 4563 (2011).

XI. 10. K. J. Strauss and S. C. Kaste, "The ALARA (As Low As Reasonably Achievable) Concept in Pediatric Interventional and Fluoroscopic Imaging: Striving to Keep Radiation Doses as Low as Possible during Fluoroscopy of Pediatric Patients—A White Paper Executive Summary," Radiology 240(3), 621-622 (2006).

XII. 11. K. Tsiklakis, C. Donta, S. Gavala, K. Karayianni, V. Kamenopoulou, and C. J. Hourdakis, "Dose reduction in maxillofacial imaging using low dose cone beam CT," European Journal of Radiology 56(3), 413-7 (2005).

XIII. 12. J. Wang, T. Li, Z. Liang, and L. Xing, "Dose reduction for kilovotage cone-beam computed tomography in radiation therapy," Physics in Medicine and Biology 53(11), 2897 (2008).

XIV. 13. J. R. Mayo et al., "Simulated dose reduction in conventional chest CT: validation study," Radiology 202 (2), 453-457 (1997).

XV. 14. D. P. Frush et al., "Computer-simulated radiation dose reduction for abdominal multidetector CT of pediatric patients," American Journal of Roentgenology 179 (5), 1107-1113 (2002).

XVI. 15. R. E. van Gelder et al., "CT Colonography at Different Radiation Dose Levels: Feasibility of Dose Reduction," Radiology 224(1), 25-33 (2002).

XVII. 16. K. Hanai et al., "Computer-simulation technique for low dose computed tomographic screening," Journal of computer assisted tomography 30(6), 955-61 (2006).

XVIII. 17. W. J. H. Veldkamp, L. J. M. Kroft, J. P. A. van Delft, and J. Geleijns, "A technique for simulating the effect of dose reduction on image quality in digital chest radiography," Journal of digital imaging 22(2), 114-25 (2009).

XIX. 18. P. Massoumzadeh, S. Don, C. F. Hildebolt, K. T. Bae, and B. R. Whiting, "Validation of CT dose-reduction simulation," Medical Physics 36(1), 174 (2009).

XX. 19. T. M. Benson and B. K. B. De Man, "Synthetic CT noise emulation in the raw data domain," in *Nuclear Science Symposium Conference Record (NSS/MIC)*, 2010 IEEE (IEEE, 2010), pp. 3169-3171.

XXI. 20. R. M. S. Joemai, J. Geleijns, and W. J. H. Veldkamp, "Development and validation of a low dose simulator for computed tomography," European radiology 20(4), 958-66 (2010).

XXII. 21. M. Söderberg, M. Gunnarsson, and M. Nilsson, "Simulated dose reduction by adding artificial noise to measured raw data: a validation study," Radiation protection dosimetry 139(1-3), 71-7 (2010).

XXIII. 22. L. Yu, M. Shiung, D. Jondal, and C. H. McCollough, "Development and validation of a practical lower-dose-simulation tool for optimizing computed tomography scan protocols," Journal of computer assisted tomography 36(4), 477-87 (2012).

XXIV. 23. S. abić, Q. Wang, T. Morton, and K. M. Brown, "A low dose simulation tool for CT systems with energy integrating detectors," Medical Physics 40, 31102 (2013).

XXV. 24. A. S. Wang and N. J. Pelc, "Synthetic CT: Simulating arbitrary single and dual energy protocols from a dual energy scan," Medical Physics 38(10), 5551-5562 (2011).

XXVI. 25. A. J. Britten, "The addition of computer simulated noise to investigate radiation dose and image quality in images with spatial correlation of statistical noise: an example application to X-ray CT of the brain," British Journal of Radiology 77(916), 323-328 (2004).

XXVII. 26. A. S. Wang, C. Feng, and N. J. Pelc, "Image-based synthetic CT: simulating arbitrary low dose single and dual energy protocols from dual energy images," in *Proceedings of SPIE* (2012), p. 83131G.

XXVIII. 27. C. Won Kim and J. H. Kim, "Realistic simulation of reduced-dose CT with noise modeling and sinogram synthesis using DICOM CT images," Medical Physics 41(1), 011901 (2014).

XXIX. 28. J. H. Siewerdsen, L. E. Antonuk, Y. El-Mohri, J. Yorkston, W. Huang, and I. A. Cunningham, "Signal, noise power spectrum, and detective quantum efficiency of indirect-detection flat-panel imagers for diagnostic radiology," Medical Physics 25(5), 614 (1998).

XXX. 29. D. J. Tward and J. H. Siewerdsen, "Cascaded systems analysis of the 3D noise transfer characteristics of flat-panel cone-beam CT," Medical Physics 35(12), 5510 (2008).

XXXI. 30. S.-J. Tu, C. C. Shaw, and L. Chen, "Noise simulation in cone beam CT imaging with parallel computing," Physics in medicine and biology 51(5), 1283-97 (2006).

XXXII. 31. A. Macovski, *Medical Imaging Systems* (Prentice-Hall, 1983).

XXXIII. 32. H. H. Barrett and K. J. Myers, *Foundations of Image Science* (Wiley-Interscience, Hoboken, N.J., 2003).

XXXIV. 33. N. Navab et al., "Dynamic geometrical calibration for 3D cerebral angiography," in *Proceedings of SPIE* (1996), p. 361.

XXXV. 34. R. R. Galigekere, K. Wiesent, and D. W. Holdsworth, "Cone-beam reprojection using projection-matrices," Medical Imaging, IEEE Transactions on 22(10), 1202-1214 (2003).

XXXVI. 35. M. J. Daly, J. H. Siewerdsen, Y. B. Cho, D. A. Jaffray, and J. C. Irish, "Geometric calibration of a mobile C-arm for intraoperative cone-beam CT," Medical physics 35, 2124 (2008).

XXXVII. 36. C. Schmidgunst, D. Ritter, and E. Lang, "Calibration model of a dual gain flat panel detector for 2D and 3D x-ray imaging," Medical physics 34, 3649 (2007).

XXXVIII. 37. A. S. Wang et al., "Soft-tissue imaging with C-arm cone-beam CT using statistical reconstruction," Physics in Medicine and Biology 59(4), 1005-1029 (2014).

XXXIX. 38. E. Y. Sidky and X. Pan, "Image reconstruction in circular cone-beam computed tomography by constrained, total-variation minimization," Physics in medicine and biology 53(17), 4777-807 (2008).

XL. 39. Jing Wang, Tianfang Li, Hongbing Lu, and Zhengrong Liang, "Penalized weighted least-squares approach to sinogram noise reduction and image reconstruction for low-dose X-ray computed tomography," IEEE Transactions on Medical Imaging 25(10), 1272-1283 (2006).

XLI. 40. J. Tang, B. E. Nett, and G.-H. Chen, "Performance comparison between total variation (TV)-based compressed sensing and statistical iterative reconstruction algorithms," Physics in Medicine and Biology 54(19), 5781 (2009).

XLII. 41. X. Jia, B. Dong, Y. Lou, and S. B. Jiang, "GPU-based iterative cone-beam CT reconstruction using tight frame regularization," Physics in Medicine and Biology 56(13), 3787 (2011).

XLIII. 42. M. Wu and J. A. Fessler, "GPU acceleration of 3D forward and backward projection using separable footprints for X-ray CT image reconstruction," in *Proc. of Fully 3D Image Reconstruction* (2011), pp. 56-59.

XLIV. 43. Y. Long, J. A. Fessler, and J. M. Balter, "3D forward and back-projection for X-ray CT using separable footprints," Medical Imaging, IEEE Transactions on 29(11), 1839-1850 (2010).

XLV. 44. B. De Man and S. Basu, "Distance-driven projection and backprojection in three dimensions," Physics in Medicine and Biology 49(11), 2463 (2004).

XLVI. 45. R. L. Siddon, "Prism representation: a 3D ray-tracing algorithm for radiotherapy applications," Physics in Medicine and Biology 30(8), 817 (1985).

XLVII. 46. L. A. Feldkamp, L. C. Davis, and J. W. Kress, "Practical cone-beam algorithm," JOSA A 1(6), 612-619 (1984).

XLVIII. 47. H. Erdogan and J. A. Fessler, "Ordered subsets algorithms for transmission tomography," Physics in Medicine and Biology 44(11), 2835-2851 (1999).

XLIX. 48. H. Erdogan and J. A. Fessler, "Monotonic algorithms for transmission tomography," IEEE Transactions on Medical Imaging 18(9), 801-814 (1999).

L. 49 S. J. Riederer, N. J. Pelc, and D. A. Chesler, "The noise power spectrum in computed X-ray tomography," Physics in Medicine and Biology 23(3), 446-454 (1978).

LI. 50. M. F. Kijewski and P. F. Judy, "The noise power spectrum of CT images," Physics in Medicine and Biology 32(5), 565-575 (1987).

LII. 51. J. H. Siewerdsen, I. A. Cunningham, and D. A. Jaffray, "A framework for noise-power spectrum analysis of multidimensional images," Medical Physics 29(11), 2655 (2002).

LIII. 52. J. W. Stayman, Y. Otake, J. L. Prince, A. J. Khanna, and J. H. Siewerdsen, "Model-based tomographic reconstruction of objects containing known components," IEEE transactions on medical imaging 31(10), 1837-48 (2012).

We claim:

1. A low-dose x-ray preview image method, comprising:
performing, by at least one processor, an initial scan of a patient at a pre-selected amount of x-ray exposure with an x-ray imaging device;
creating, by the at least one processor, at least one initial image projection of said patient based on said initial scan;
injecting, by the at least one processor, correlated noise into said at least one initial image projection of said initial scan of said patient;
reconstructing, by at least one processor, said at least one initial image projection according to an algorithm specific to a task of said patient and based of said detected signal and said injecting of said correlated noise;
displaying, by at least one processor, at least one low-dose preview image based on said reconstruction of said at least one initial image projection according to an algorithm specific to a task of said patient and based on said detected signal and said injecting of said correlated noise; and
enabling, by at least one processor, a selection of said at least one low-dose preview image based on said at least one initial image projection according to an algorithm specific to a task of said patient and based on said detected signal and said injecting of said correlated noise for at least one subsequent scan.

2. A low-dose x-ray preview image method according to claim 1, wherein said correlated noise represents a lower amount of x-ray exposure than said initial scan of said patient at said pre-selected amount of x-ray exposure.

3. A low-dose x-ray preview image method according to claim 2, wherein each of said at least one low-dose preview image represents at least one of a variation of detector blur and a variation of detector gain.

4. A low-dose x-ray preview image method according to claim 1, wherein each of said at least one initial preview image are injected with a varying amount of said correlated noise.

5. A low-dose x-ray preview image method according to claim 1, wherein said at least one low-dose preview image is a preview of at least one of a radiographic image, a fluoroscopic image, a tomosynthesis reconstruction, a computed tomography reconstruction, and a cone-beam computed tomography reconstruction.

6. A low-dose x-ray preview image method according to claim 1, wherein the correlated noise includes at least one of a quantum noise and an electronic noise.

7. A low-dose x-ray preview image method according to claim 1, wherein said reconstruction includes at least one of a filtered backprojection and a model-based image reconstruction.

8. A low-dose x-ray preview image method according to claim 1, wherein said reconstruction discards said at least one initial image projection of said patient based on said initial scan.

9. A low-dose x-ray preview image method according to claim 1, wherein said x-ray imaging device includes at least an emitter and a detector.

10. A low-dose x-ray preview image method according to claim 9, wherein said detector is a flat panel detector.

11. A low-dose x-ray preview image device, comprising:
an x-ray imaging device;
at least one storage unit in communication with said x-ray imaging device;
at least one data processor in communication with said at least one storage unit and said x-ray imaging device; and
at least one display device in communication with said at least one storage unit and said at least one data processor;
wherein said at least one processor is configured to:
perform an initial scan of a patient at a pre-selected amount of x-ray exposure with said x-ray imaging device;
create at least one initial preview image of said patient based on said initial scan;
inject correlated noise into said at least one initial image projection of said initial scan of said patient;
reconstruct said at least one initial image projection according to an algorithm specific to a task of said patient and based on said detected signal and said injecting of said correlated noise;
display, at said at least one display device, an at least one low-dose preview image based on said reconstruction of said at least one initial image projection according to an algorithm specific to a task of said patient and based on said detected signal and said injecting of said correlated noise; and
enable, at said at least one display device, a selection of said at least one low-dose preview image based on said at least one initial image projection according to an algorithm specific to a task of said patient and based on said detected signal and said injecting of said correlated noise for at least one subsequent scan.

12. A low-dose x-ray preview image device according to claim 11, wherein said correlated noise represents a lower amount of x-ray exposure than said initial scan of said patient at said pre-selected amount of x-ray exposure.

13. A low-dose x-ray preview image device according to claim 12, wherein each of said at least one low-dose preview image represents at least one of a variation of detector blur and a variation of detector gain.

14. A low-dose x-ray preview image device according to claim 11, wherein each of said at least one initial image projection are injected with a varying amount of said correlated noise.

15. A low-dose x-ray preview image device according to claim 11, wherein said at least one low-dose preview image is a preview of at least one of a radiographic image, a fluoroscopic image, a tomosynthesis reconstruction, a computed tomography reconstruction, and a cone-beam computed tomography reconstruction.

16. A low-dose x-ray preview image device according to claim 11, wherein the correlated noise includes at least quantum noise and an electronic noise.

17. A low-dose x-ray preview image device according to claim 11, wherein said reconstruction includes at least one of a filtered backprojection and a model-based image reconstruction.

18. A low-dose x-ray preview image device according to claim 11, wherein said reconstruction discards said at least one initial image projection of said patient based on said initial scan.

19. A low-dose x-ray preview image device according to claim 11, wherein said low-dose x-ray image projection device includes at least an emitter and detector.

20. A low-dose x-ray image projection device according to claim 19, wherein said detector is a flat panel detector.

21. A non-transitory computer readable medium comprising software, which when executed by a computer, causes the computer to:
    perform, by at least one processor, an initial scan of a patient at a pre-selected amount of x-ray exposure with an x-ray imaging device;
    create, by the at least one processor, at least one initial image projection of said patient based on said initial scan;
    inject, by the at least one processor, correlated noise into said at least one initial image projection of said initial scan of said patient;
    reconstruct, by at least one processor, said at least one initial image projection according to an algorithm specific to a task of said patient and based said detected signal and said injecting of said correlated noise;
    display, by at least one processor, at least one low-dose preview image based on said reconstruction of said at least one initial image projection according to an algorithm specific to a task of said patient and based on said detected signal and said injecting of said correlated noise; and
    enable, by at least one processor, a selection of said at least one low-dose preview image based on said at least one initial image projection according to an algorithm specific to a task of said patient and based on said detected signal and said injecting of said correlated noise for at least one subsequent scan.

22. A non-transitory computer readable medium according to claim 21, wherein said correlated noise represents a lower amount of x-ray exposure than said initial scan of said patient at said pre-selected amount of x-ray exposure.

23. A non-transitory computer readable medium according to claim 22, wherein each of said at least one low-dose preview image represents at least one of a variation of detector blur and a variation of detector gain.

24. A non-transitory computer readable medium according to claim 21, wherein each of said at least one initial image projection are injected with a varying amount of said correlated noise.

25. A non-transitory computer readable medium according to claim 21, wherein said at least one low-dose preview image is a preview of at least one of a radiographic image, a fluoroscopic image, a tomosynthesis reconstruction, a computed tomography reconstruction, and cone-beam computed tomography reconstruction.

26. A non-transitory computer readable medium according to claim 21, wherein said reconstruction discards said at least one initial image projection of said patient based on said initial scan.

27. A non-transitory computer readable medium according to claim 21, wherein the correlated noise includes at least one of a quantum noise and an electronic noise.

28. A non-transitory computer readable medium according to claim 21, wherein said reconstructing includes at least one of a cone-beam filtered backprojection and a model-based image reconstruction.

29. A non-transitory computer readable medium according to claim 21, wherein said x-ray imaging device includes at least an emitter and a detector.

30. A non-transitory computer readable medium according to claim 29, wherein said detector is a flat panel detector.

* * * * *